(12) United States Patent
Dicke et al.

(10) Patent No.: US 8,569,423 B2
(45) Date of Patent: Oct. 29, 2013

(54) TRIAZINE DERIVATIVES AND A METHOD FOR THEIR PRODUCTION

(75) Inventors: Rene Dicke, Leonding (AT); Martin Burger, Linz (AT); Christoph Hahn, Linz (AT); Andreas Endersfelder, Linz (AT); Clemens Schwarzinger, Wels (AT); Klaus Bretterbauer, Linz (AT); Harald Schmidt, Linz (AT)

(73) Assignee: Borealis Agrolinz Melamine GmbH, Linz (AT)

( * ) Notice: Subject to any disclaimer, the term of this patent is extended or adjusted under 35 U.S.C. 154(b) by 974 days.

(21) Appl. No.: 12/599,243

(22) PCT Filed: May 29, 2008

(86) PCT No.: PCT/EP2008/056633
§ 371 (c)(1),
(2), (4) Date: Nov. 6, 2009

(87) PCT Pub. No.: WO2008/145704
PCT Pub. Date: Dec. 4, 2008

(65) Prior Publication Data
US 2010/0292409 A1    Nov. 18, 2010

(51) Int. Cl.
C08F 8/32    (2006.01)
(52) U.S. Cl.
USPC .................................................... 525/330.5
(58) Field of Classification Search
USPC .................................................... 525/330.5
See application file for complete search history.

(56) References Cited

U.S. PATENT DOCUMENTS

| | | | |
|---|---|---|---|
| 2,394,042 A | 2/1946 | D'Alelio | |
| 4,007,032 A | 2/1977 | Berrer | |
| 4,732,899 A | 3/1988 | Gehret et al. | |
| 5,084,541 A | 1/1992 | Jacobs, III et al. | |
| 5,705,641 A | 1/1998 | Flood et al. | |
| 6,063,922 A | 5/2000 | Flood et al. | |
| 6,204,381 B1 | 3/2001 | Zhao | |
| 2004/0249149 A1 | 12/2004 | Schneider et al. | |
| 2006/0004005 A1 | 1/2006 | Sattigeri et al. | |
| 2006/0069254 A1 | 3/2006 | Schneider et al. | |
| 2007/0083047 A1* | 4/2007 | Schneider et al. | 544/204 |
| 2007/0196668 A1 | 8/2007 | Heischkel et al. | |
| 2007/0208101 A1 | 9/2007 | Heischkel et al. | |
| 2007/0209553 A1 | 9/2007 | Wagner et al. | |

FOREIGN PATENT DOCUMENTS

| | | |
|---|---|---|
| DE | 102004018543 A1 | 11/2005 |
| EP | 0226536 A2 | 11/1986 |
| EP | 0366884 A2 | 8/1989 |
| WO | 03035628 A1 | 5/2003 |
| WO | 2004054990 A2 | 7/2004 |
| WO | 2005030735 A1 | 4/2005 |
| WO | 2005100326 A1 | 10/2005 |
| WO | 2005100328 A1 | 10/2005 |
| WO | 2005103016 A1 | 11/2005 |

OTHER PUBLICATIONS

Hirschberg, et al., Nature, "Helical Self-Assembled Polymers from Cooperative Stacking of Hydrogen-Bonded Pairs", vol. 407, Sep. 14, 2000, pp. 167-170.*

"2, 4, 6-triureido-1, 3, 5-triazine", CrossFire Beilstein Database, Beilstein Institute for Organic Chemistry, 2007-2008, Elsevier Information Systems GmbH, Frankfurt-Main, Germany.

Iio et al., "Studies of Cyanamide Derivatives. Part 110. A Facile Synthesis of 2,4,6-Triureido-1,3,5-triazine and 2-Amino-4,6-diureido-1,3,5-triazine", Bulletin of the Chemical Society of Japan, 1984, pp. 2009-2010, vol. 57, No. 7.

* cited by examiner

*Primary Examiner* — Ling Choi
*Assistant Examiner* — Lanee Reuther
(74) *Attorney, Agent, or Firm* — The Webb Law Firm

(57) ABSTRACT

The present invention relates to triazine derivatives of the general formula (I), their use and production.

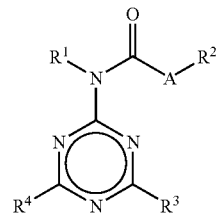

38 Claims, No Drawings

TRIAZINE DERIVATIVES AND A METHOD FOR THEIR PRODUCTION

BACKGROUND OF THE INVENTION

1) Field of the Invention

The invention relates to triazine derivatives, in particular modified triazine carbamates and triazine ureas, a method for their production and their use.

2) Description of the Related Art

U.S. Pat. No. 5,084,541 describes tricarbamoyl triazines (triazine tricarbamates, melamine tricarbamates), which can be synthesized starting from triazine triisocyanurates by conversion with different alcohols. These always three times substituted products can be for instance used as cross linking agents.

U.S. Pat. No. 6,063,922 describes triazine carbamates, which are formed by conversion with melamine and acyclic organic carbonates in the presence of strong bases. Thereby, bi- or tricarbamates are always formed.

EP 0 366 884 A2 describes triazine compounds with at least one carbamyl group, whereby the carbamyl group is separated by at least one methylen group from the amino group of triamino triazine. Also products of melamine and formaldehyde are included in the compounds of EP 0 366 884 A2.

DE 10 2004 018 543 A1 also describes carbamate group containing triazine derivatives, which serve as cross linking agents for lacquers with improved properties.

WO 2005/103016 A1 describes radiation curable triazine carbamates and triazine ureas, which are halogen-free and contain vinyl, methacrylolyl or acrylolyl groups.

SUMMARY OF THE INVENTION

The object of the invention is to provide triazine derivatives, which can be adjusted in their viscosity or their melting properties in contrast to the known compounds.

DETAILED DESCRIPTION OF THE PREFERRED EMBODIMENTS

This problem is solved by triazine derivatives according to formula (I) according to claim 1. Such triazine derivatives, in particular modified melamine carbamates and melamine ureas as well as guanamine carbamates and guanamine ureas, have a structure of the general formula (I)

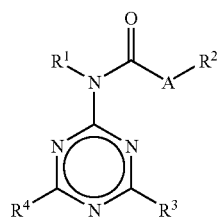
(I)

wherein $R^3$ means $Q^1$ or a moiety of the formula $R^5$—N—$R^6$ connected with its central nitrogen atom to the triazine ring

of the structure of formula (I), wherein $Q^1$ means a linear or branched $C_1$-$C_{50}$-alkyl or a cyclic substituent in form of a $C_5$-$C_{20}$-cycloalkyl, a $C_5$-$C_{20}$-aryl, a $C_1$-$C_{20}$-alkyl substituted $C_5$-$C_{20}$-aryl, a $C_2$-$C_{20}$-alkenyl substituted $C_5$-$C_{20}$-aryl or of an imide of a cyclic saturated or unsaturated carboxylic acid, wherein the $C_1$-$C_{50}$-alkyl or the cyclic substituent can be interrupted by one or multiple oxygen atoms, sulphur atoms, substituted and/or unsubstituted nitrogen atoms and/or by one or multiple groups of the type —C(O)O—, —OC(O)—, —C(O)—, —NHC(O)O—, —OC(O)NH— and/or —OC(O)O—, $R^4$ means $Q^1$ or a moiety of the formula $R^7$—N—$R^8$ connected with the nitrogen atom to the triazine ring of the structure of the formula (I), $R^1$, $R^5$, and $R^7$ mean independently from each other H or $Q^2$, wherein $Q^2$ means in each case a linear or branched $C_1$-$C_{50}$-alkyl, $C_5$-$C_{20}$-cycloalkyl, $C_5$-$C_{20}$-aryl, $C_1$-$C_{20}$-alkyl substituted $C_5$-$C_{20}$-aryl, $C_2$-$C_{20}$-alkenyl or $C_2$-$C_{20}$-alkenyl substituted $C_5$-$C_{20}$-aryl, that in each case can be interrupted by one or multiple oxygen atoms, sulphur atoms, substituted and/or unsubstituted nitrogen atoms and/or by one or multiple groups of the type —C(O)O—, —OC(O)—, —C(O)—, —NHC(O)O—, —OC(O)NH— and/or —OC(O)O—, A means —O—, —NH—, —$NR^2$—, —$NR^{62}$— or —$NR^{82}$—, in particular only —$NR^2$—, $R^6$ and $R^8$ mean independent from each other H, $Q^2$-CO-A-$R^2$, —CO-A-$R^{61}$, —CO-A-$R^{81}$, in particular only —CO-A-$R^2$, $R^2$, $R^{61}$, $R^{62}$, $R^{81}$ and $R^{82}$ mean in dependent from each other $Q^2$, a moiety of a substituted or non-substituted alcohol, a moiety of a substituted or unsubstituted polyvalent alcohol, a moiety of an amine, a moiety of an amino alcohol, a moiety of a diamine or a moiety of the general formula (II),

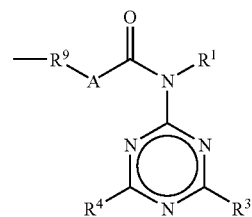
(II)

whereby $R^9$ means $Q^2$, with the stipulation that in case $R^3$ means $R^5$—N—$R^6$ and $R^4$ means $R^7$—N—$R^8$, at least one of the moieties $R^1$, $R^5$, and $R^7$ means $Q^2$ and is bound to a nitrogen atom that is covalently connected to the moiety —CO-A-$R^2$, —CO-A-$R^{61}$ or —CO-A-$R^{81}$ (this means that this nitrogen atom is in particular part of a carbamat group), or at least the moieties $R^5$ and $R^6$ on the one hand and the moieties $R^7$ and $R^8$ on the other hand mean in each case $Q^2$ (thus, at least two moities of the type $Q^2$ are bound to one and the same nitrogen atom) or at least one of the moieties $R^5$ or $R^6$ means $Q^2$ and $R^7$ and $R^8$ mean both simultaneously H.

The object of the invention is likewise solved by compositions of the general formula (I) of the corresponding triazine derivatives.

In the context of the invention only such a hydrogen carbon moiety is to be understood as a linear or branched hydrogen carbon moiety interrupted by any group (like in particular $C_1$-$C_{50}$-alkyl, $C_5$-$C_{20}$-cycloalkyl, $C_5$-$C_{20}$-aryl, $C_1$-$C_{20}$-alkyl substituted $C_5$-$C_{20}$-aryl, $C_2$-$C_{20}$-alkenyl or $C_2$-$C_{20}$-alkenyl substituted $C_5$-$C_{20}$-aryl) which does not carry the corresponding group on one of its ends. The hydrogen carbon chain has rather to be in fact interrupted by the group.

This means, that the moiety $Q^1$ is immediately bound to the triazine ring with a (unsubstituted) carbon atom, if it represents a linear or branched $C_1$-$C_{50}$-alkyl. Since cyclic substituents do not have ends in the usual sense, these cyclic substituents can be bound to the triazine ring with one oxygen atom sulphur atom, nitrogen atom or with the group of the type —C(O)O—, —OC(O)—, —C(O)—, —NHC(O)O—, —OC(O)NH— or —OC(O)O—.

A distinctive feature of the triazine derivatives according to the invention is to be seen in the fact that in presence of three, optionally derivatized, amino groups bound to the triazine ring, e.g. if the moiety $R^3$ has the meaning of $R^5$—N—$R^6$ and the moiety $R^4$ has the meaning of $R^7$—N—$R^8$, at least one of the total of five possible hydrogen atoms on the three amino groups is substituted by a carbon hydrogen unit of the type $Q^2$, whereby the introduced substituent $Q^2$ is bound to a nitrogen atom, which is covalently bound to the moiety —CO-A-$R^2$, —CO-A-$R^{61}$ or —CO-A-$R^{81}$, this is therefore arranged adjacent to a carbonyl group.

A further distinctive feature of the triazine derivatives according to the invention is to be seen in the fact that instead of one or two optionally substituted amino groups as moieties $R^3$ and $R^4$ also one or two $C_1$-$C_{50}$-alkyl groups or cyclic substituents (or a mixture of both types of substituents) which also contain a carbon hydrogen unit, can be bound to the triazine ring, so that also in this manner an increased carbon hydrogen proportion in contrast to a hydrogen atom as a part of an optionally one time substituted amino group can be introduced in the triazine derivative according to the invention. In this manner, for instance, benzoguanamine or acetoguanamine derivatives can be provided.

A further characteristic of the triazine derivatives according to the invention is also to be seen in the fact that, if the moiety $R^3$ has the meaning of $R^5$—N—$R^6$ and the moiety $R^4$ has the meaning of $R^7$—N—$R^8$, either $R^5$ and $R^6$ mean in each case $Q^2$ or $R^7$ and $R^8$ mean in each case $Q^2$. Also in this manner the carbon hydrogen proportion in the triazine derivatives can be increased.

A further feature of the triazine derivatives according to the invention is also to be seen in the fact that, if the moiety $R^3$ has the meaning $R^5$—N—$R^6$ and the moiety $R^4$ has the meaning $R^7$—N—$R^8$, at least $R^5$ or $R^6$ means $Q^2$ and $R^7$ and $R^8$ mean both simultaneously H. This means, an amino group directly bound to the triazine ring is unsubstituted, while a second amino group directly bound to the triazine ring has at least to be once substituted. This is a further possibility to increase the carbon hydrogen proportion in the triazine derivatives.

Due to the substitution of hydrogen atoms of the triazine derivatives by carbon units the hydrogen bonding system of the triazine derivatives is disturbed. In this manner the melting properties and the viscosities of the triazine derivatives according to the invention can be preferably—depending on the selected substituents—adjusted. In case of lower contents of hydrogen bonds the triazine derivatives show lower melting points or viscosities. It is also possible to obtain liquid compounds with a very low content of hydrogen bonds.

The adhesion of the triazine derivatives according to the invention on different substrates, as for instance on wood, plastics, metal, paper or textiles is improved by the direct substitution of single hydrogen atoms of the triazine compounds by organic moieties.

Depending on length, type and number of the carbon units used as (cyclic) substituents also the hydrophilic and hydrophobic properties of the triazine derivatives can preferably be modified in order to achieve an improved miscibility of the triazine derivatives according to the invention with substances of other compound classes until achieving solubility in such compounds of other compound classes. This means, the compatibility of the triazine derivatives to other compounds is influenced by the election of one or multiple substituents. A substituent in form of a $C_6$-$C_{12}$-alkyl chain for instance leads to an improved miscibility of the corresponding triazine derivative with alkyd resins. Furthermore, amino groups prolonged with ethylene glycol units show for instance a better miscibility with polyether polyoles.

Thereby, the length of the applied carbon chain plays in particular an important role for the hydrophobicity of the substituents and in particular the type and number of the atoms or groups of a polar character interrupting the carbon chain play an important role for the hydrophilicity of the substituents. The respective resulting van-der-Waals and hydrophobic interactions as well as a number of the formed hydrogen bonds influence significantly the viscosity and the melting behaviour of the triazine derivatives. Even though a reduction of viscosity or the melting point is in general preferred, an increase of the viscosity or the melting point in contrast to the compounds known from the prior art is conceivable by introducing carbon hydrogen moieties which have a number of polar groups, for instance —C(O)O—, —OC(O)—, —O(O)—, —NHC(O)O—, —OC(O)NH— and/or —OC(O)O— and therefore allow an increased hydrogen bond formation.

In an embodiment the moieties $R^{61}$, $R^{62}$, $R^{81}$ and $R^{82}$ can correspond to the moiety $R^2$, respectively.

It is preferred, if at least one of the moieties $R^1$, $R^5$, $R^6$, $R^7$, and $R^8$ mean independently on the meaning of the moieties $R^3$ and $R^4$, $Q^2$ whereby also two, three, four or all moieties can have the meaning of $Q^2$.

In a preferred embodiment of the invention at least one of the moieties $R^1$, $R^5$ and $R^7$ mean $Q^2$ independent on the meaning of the moieties $R^3$ and $R^4$, whereby the at least one moiety having the meaning of $Q^2$ is simultaneously bound to a nitrogen atom, which is covalently linked to the moiety —CO-A-$R^2$, —CO-A-$R^{61}$ or —CO-A-$R^{81}$. This meaning and chemical surrounding can have also two or three of the moieties $R^1$, $R^5$ and $R^7$.

Preferably, at least one of the moieties $R^5$, $R^6$, $R^7$ and $R^8$ mean $Q^2$ independently on the meaning of the moieties $R^3$ and $R^4$. Also two, three or all these moieties can have this exclusive meaning of $Q^2$ for $R^5$, $R^6$, $R^7$ or $R^8$.

The cyclic substituent which can be depicted by the moieties $R^3$ and $R^4$ have preferably a nitrogen atom as part of the cyclic structure via which it is bound to the triazine ring of the structure of the formula (I). A non-limiting example of such a triazine derivative is a compound according to the formula (III):

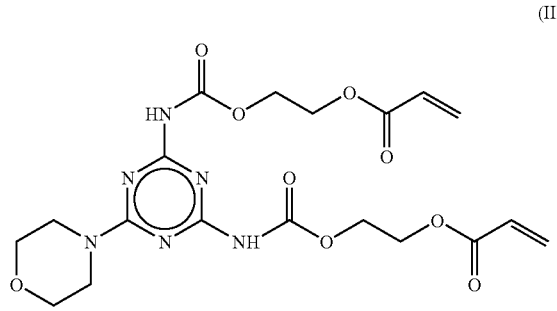

In a further preferred embodiment of the invention each of the nitrogen atoms bound to the triazine ring of the structure of the formula (I) is substituted in the same manner so that structural symmetrical triazine derivatives are provided.

The triazine derivatives according to the invention can be obtained for instance in the following process: Starting from modified melamines at first a conversion with organic carbonates occurs. Subsequently, the alkoxy terminated carbonate structure can be replaced by alcohols and/or primary or secondary amines and/or amino alcohols, if necessary. If polyvalent alcohols, amines or amino alcohols are used, the built up of linear or branched polynuclear triazine derivatives oligomers or triazine derivative polymers can occur. The used alcohols, amines or amino alcohols determine thereby the moiety $R^2$ of the structure of the formula (I).

Examples for preferably used alcohols are methanol, ethanol, propanol, isopropanol, butanol, isobutanol, pentanol, hexanol, benzylalcohol, phenol, ethylenglycolmonomethylether (2-methoxyethanol), ethylhexylalcohol, dodecylalcohol and stearyalcohol.

Further examples for preferably used substituted alcohols are 2-hydroxyethylacrylate, 2-hydroxypropylacrylate, 4-hydroxybutylacrylate, 6-hydroxyhexylacrylate, diethylenglycol-monoacrylate, triethylenglycolmonoacrylate, dipropylenglycolmonoacrylate, tripropylen-glycolmonoacrylate, trimethylolpropandiacrylate, pentaerythritdiacrylate, pentaerythrittriacrylate, 2-hydroxyethylmethacrylate, 2-hydroxypropylmethacrylate, 4-hydroxybutylmethacrylate, 6-hydroxyhexylmethacrylate, diethylenglycolmonomethacrylate, triethylenglycolmonomethacrylate, dipropylenglycolmonomethacrylate, tripropylenglycolmonomethacrylate, trimethylolpropandimethacrylate, pentaerythritdimethacrylate, pentaerythrittrimethacrylate and/or 4-hydroxybutylvinylether.

Examples for preferably used polyvalent alcohols are ethylenglycol, butandiol, octandiol, dodecandiol, octadecandiol, glycol, trimethylolpropane, pentaerythrit, polyethylenglycoles with molar masses of 200 to 5000, polypropylenglycoles with molar masses of 200 to 5000, polytetrahydrofuranes with molar masses of 200 to 5000 and/or polyesterdioles on the basis of saturated dicarboxylic acids like terephthalic acid, isophthalic acid, naphthalindicarboxylic acid, maleinic acid, fumaric acid and/or itakonic acid and diols like ethylenglycol, butandiol, neopentylglycol and/or hexandiol.

Examples for preferably used amines and diamines are ethylamine, diethylamine, propylamine, dipropylamine, isopropylamine, diisopropylamine, butylamine, dibutylamine, hexylamine, hexamethylendiamine, propylendiamine, butylendiamine and/or ethylendiamine.

Examples for preferably used amino alcohols are aminoethanol, aminopropanol, aminoethoxyethanol, diethanolamine, triethanolamine, triisopropanolamine, diisopropanolamine and/or isopropanolamine.

Preferably at least one of the moieties $R^1$, $R^5$, $R^6$, $R^7$ and $R^8$ has a $C_1$-$C_{18}$ alkyl group in order to affect in particular beneficial properties of a triazine derivative in respect to melting point and viscosity. This applies in particular to the moieties $R^1$, $R^5$ and $R^7$.

For providing modified melamine monocarbamates or modified melamine dicarbamates it is of an advantage, if the moiety $R^6$ and/or the moiety $R^8$ only have the meaning of $Q^2$, but not the meaning of CO-A-$R^2$, —CO-A-$R^{61}$ or —CO-A-$R^{81}$.

The triazine derivatives according to the invention are preferably polymerizable by radiation hardening or by radiation in dependency on the introduced groups. Thereby, the hardening/polymerization occurs preferably radically, for instance via double bounds or acidicly for instance via epoxide structures. Depending on the number of the reactive groups present in respect to a polymerization appropriate triazine derivatives can for instance be used for cross linking.

Electromagnetical radiation, for instance in form of UV radiation and particle radiation, for instance in form of electron radiation, have turned out to be the preferred radiation types for hardening or polymerization.

In a further preferred embodiment of the invention the triazine derivatives can also be brought to reaction for instance with hydroxyl terminated polyesters by condensation and/or with epoxides by addition and are therefore usable also as cross linking agent of these compound classes. An initiation of a corresponding polymerization reaction or also other polymerization reactions can for instance occur thermally and/or chemically.

Due to the adjustment of the ratio of hydrophobicity to hydrophilicity via the substitution pattern the triazine derivatives according to the invention can excellently be adapted to compounds of other compound classes. In particular by reducing the hydrogen bonds on the (in particular —CO-A-$R^2$—, —CO-A-$R^{61}$— or —CO-A-$R^{81}$-substituted) amino groups of the melamine an improved solubility is achieved so that also higher molecular compounds like oligomers and polymers can be better dissolved in other substances or compounds. Single triazine derivate monomers (or substituted melamine nuclei or substituted triazine nuclei are covalently bound to each other in oligomers or polymers.

Object of the invention are also compositions, in particular reactive compositions, of the triazine derivatives according to the invention with at least one composite, whereby urea resin, urea-melamine resin, melamine resin, melamine-phenol resin, phenol resin, polyester, polyacrylate, polyurethane, epoxide, polyether and/or a mixture of these substances are included. Thereby, such compositions are understood as reactive compositions, in which the triazine derivatives can react with the at least one composite during an application, in particular during hardening.

The triazine derivatives according to the invention and the above defined compositions can also preferably be used as cross linking agents and/or binder in coating masses, paints and lacquers. In particular, preferred applications are powder lacquers in particular due to the defined adjustment of the melting points of the triazine derivatives. But also the high number of cross linkable or cross linking groups in triazine derivatives offer advantages in respect to the properties of the triazine derivatives, in particular regarding hardness and scratch resistance.

A further preferred use of the triazine derivatives and the above defined compositions is their use as binders for composite material (compounds) and moulding masses, in foams, in fibers and in combination with further compounds (in particular synergistic agents) in fire protection equipment.

A further preferred use of the triazine derivatives and the above defined compositions is their use as cross linking agent and/or co-reactant in the production of a laminate for improving the surface properties of the laminate. In particular scratch resistance, hardness and haptics are thereby to mention as surface properties. The laminates can be preferably provided for the wood processing industry.

Object of the invention is also method for the production of triazine derivatives according to the invention. This method is characterized by A) conversion of a triazine derivative according to the general formula (IX)

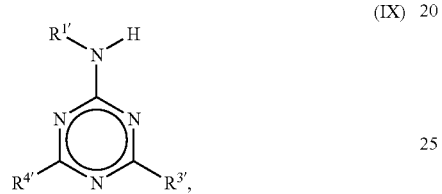

(IX)

whereby

R$^{3'}$ means Q$^1$ or a moiety of the formula R$^{5'}$—N—R$^{6'}$ bound with its central nitrogen atom to the triazine ring of the structure of the formula (IX), wherein Q$^1$ means a linear or branched C$_1$-C$_{50}$-alkyl or a cyclic substituent in form of a C$_5$-C$_{20}$-cycloalkyl, a C$_5$-C$_{20}$-aryl, a C$_1$-C$_{20}$-alkyl substituted C$_5$-C$_{20}$-aryl, a C$_2$-C$_{20}$-alkenyl substituted C$_5$-C$_{20}$-aryl or an imide of cyclic saturated or unsaturated carboxylic acids, wherein the C$_1$-C$_{50}$-alkyl or the cyclic substituent can be interrupted by one or multiple oxygen atoms, sulphur atoms, substituted and/or unsubstituted nitrogen atoms and/or by one or multiple groups of the type —C(O)O—, —OC(O)—, —C(O)—, —NHC(O)O—, —OC(O)NH— and/or —OC(O)O—, R$^{4'}$ means Q$^1$ or a moiety of the formula R$^{7'}$—N—R$^{8'}$ bound with the nitrogen atom to the triazine ring of the structure of the formula (IX), R$^{1'}$, R$^{5'}$, and R$^{7'}$ independently from each other mean H or Q$^2$, wherein Q$^2$ means in each case linear or branched C$_1$-C$_{50}$-alkyl, C$_5$-C$_{20}$-cycloalkyl, C$_5$-C$_{20}$-aryl, C$_1$-C$_{20}$-alkyl substituted C$_5$-C$_{20}$-aryl, C$_2$-C$_{20}$-alkenyl or C$_2$-C$_{20}$-alkenyl substituted C$_5$-C$_{20}$-aryl, which can be interrupted in each case by one or multiple oxygen atoms, sulphur atoms, substituted and/or unsubstituted nitrogen atoms and/or by one or multiple groups of the type —C(O)O—, —OC(O)—, —C(O)—, —NHC(O)O—, —OC(O)NH— and/or —OC(O)O—, R$^{6'}$ and R$^{8'}$ mean independently from each other H, Q$^2$, —CO-A-R$^{61}$ or —CO-A-R$^{81}$, A means —O—, —NH— or —NR$^{62}$— or —NR$^{82}$—, R$^{61}$, R$^{62}$, R$^{81}$ and R$^{82}$ mean independently from each other Q$^2$, a moiety of a substituted or unsubstituted alcohol, a moiety of the substituted or unsubstituted polyvalent alcohol, a moiety of an amine, a moiety of an amino alcohol, a moiety of a diamine or a moiety of the general formula (II)

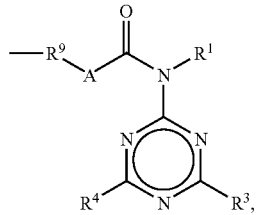

(II)

whereby R$^9$ means Q$^2$, with phosgen and

B) a further conversion of the carbamoylchloride of the triazine derivative formed in step A) with a substituted or unsubstituted alcohol of the general formula R$^2$—OH, a substituted or unsubstituted polyvalent alcohol of the general formula R$^2$—(OH)$_n$ with n≥2, an amine of the general formula R$^2$—NH$_2$ or R$^2$—NH—R$^{20}$, an amino alcohol of the general formula OH—R$^2$—NH$_2$ or R$^2$—NH—R$^{20}$—OH, a diamine of the general formula R$^2$—(NH$_2$)$_2$ or a moiety of the general formula (II), whereby R$^2$ and R$^{20}$ mean independently from each other Q$^2$, a moiety of a substituted or unsubstituted alcohol, a moiety of a substituted or unsubstituted polyvalent alcohol, a moiety of an amine, a moiety of an amino alcohol, a moiety of a diamine or a moiety of the general formula (II).

The conversion of the carbamoyl chloride of the triazine derivative formed in step A) with an alcohol, amine, diamine or amino alcohol occurs preferably immediately, that means without isolation of the intermediate product.

The optional substituents of the applied alcohols, amines, diamines or amino alcohols are preferably one or multiple further OH- and/or NH- and/or NH$_2$-groups. For instance alcohols, amines, diamines are amino alcohols in which R$^2$ and/or R$^{20}$ independently from each other mean Q2 and which have one or multiple further OH- and/or NH- and/or NH$_2$-groups, can be applied.

In respect to the preferably used alcohols, amines and amino alcohols it is referred to the above explanations in respect to a further method of production, which are also valid for the method described here. Regarding further preferred meanings of the respective moieties it is referred to the above explanation to the triazine derivatives according to the invention, which also apply in analogy to the method of production.

After completion of the reaction the formed triazine carbamate can be further modified by conversion with an substituted or unsubstituted alcohol of the general formula R$^2$—OH, a substituted or unsubstituted polyvalent alcohol of the general formula R$^2$—(OH)$_n$ with n≥2, an amine of the general formula R$^2$—NH$_2$ or R$^2$—NH—R$^{20}$, an amino alcohol of the general formula OH—R$^2$—NH$_2$ or R$^2$—NH—R$^{20}$—OH, a diamine of the general formula R$^2$—(NH$_2$)$_2$. The moieties R$^2$ and R$^{20}$ can thereby have independently from each other the above-mentioned meanings, whereby preferably one reactant with a different R$^2$ than during the production of the triazine derivatives is used.

In this manner, the moiety R$^2$ of the triazine derivative can be replaced (analogue to re-etherification). By using polyvalent alcohols, amines or amino alcohols the built-up of linear or branched polynuclear triazine derivative oligomers or triazine derivative polymers can occur.

The conversion of the triazine derivative with phosgene in step A) of the process is carried out preferably in an inert gas atmosphere at temperatures of ca. −20° C. to ca. +80° C., whereby preferably an excess of phosgene is used. At first, (for mixing the triazine derivative educt with phosgene) the reaction is in particular carried out at lower temperatures in the area of ca. −10° C. to ca. +30° C., in particular ca. 0° C. to ca. +20° C. or to ca. +25° C. and thereafter the temperature is increased for the actual reaction to ca. 40° C. to ca. 70° C., in particular ca. 50° C. to ca. 60° C.

After completion of the reaction, the excess of phosgene is driven out by heating to temperatures of ca. 100° C. to ca. 200° C., in particular, ca. 110° C. to 150° C. and especially particular ca. 120° C. to ca. 140° C.

The conversion of the formed carbamoyl chloride of the triazine derivative with the alcohol $R^2$—OH or $R^2$—$(OH)_n$ with n≥2, the amine $R^2$—$NH_2$ or $R^2$—NH—$R^{20}$, the amino alcohol OH—$R^2$—$NH_2$ or $R^2$—NH—$R^{20}$—OH or the diamine $R^2$—$(NH_2)_2$ occurs at a temperature of ca. +50° C. to ca. 150° C., preferably at ca. 60° C. to ca. 100° C., in particular preferably at ca. 70° C. to ca. 90° C., advantageously in an inert gas atmosphere. The formed hydrogen chloride can be driven out by an inert gas stream.

The reaction is in particular carried out in solution, whereby preferably chlorbenzol, nitrobenzol, dichlorbenzol and dioxane are used as solvents.

The following examples describe the production of embodiments of the triazine derivatives according to the invention.

Example 1

0.5 mol N,N′,N″-trimethyl melamine are provided with 12 molar equivalents dimethylcarbonate in a flask and heated to 70° C. 11 Molar equivalents natrium methanolate are dissolved in 2 l methanol and are added dropwise to the mixture via a dropping funnel. After the addition it is stirred 120 min under reflux and subsequently cooled down and neutralized with aqueous phosphoric acid. The precipitated product is being sucked off and dried. After analysis by HPLC a content of 94% N,N′,N″-trimethyl-N,N′,N″-tris(methoxycarbonyl)-melamine of the following formula (IV) is determined:

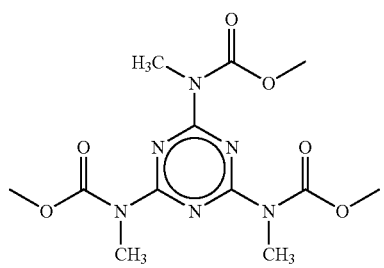

(IV)

Example 2

0.5 mol N,N-dimethylmelamine are provided with 8 molar equivalents dimethylcarbonate in a flask and heated to 70° C. 7 Molar equivalents natrium methanolate are dissolved in 2 l methanol and are added dropwise into the mixture via a dropping funnel. After the addition it is stirred 90 min under reflux and subsequently cooled down and neutralized with aqueous phosphoric acid. The precipitated product is sucked off and dried. After analysis by HPLC a content of 98% N,N-dimethyl-N′,N″-di-(methoxycarbonyl)-melamine of the following formula (V) is determined:

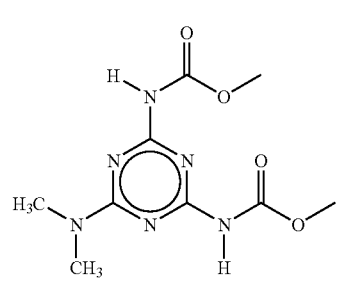

(V)

Example 3

0.5 mol N-Monomethyl melamine is provided with 12 molar equivalents dimethylcarbonate in a flask and heated to 70° C. 11 Molar equivalents natriummethanolate are dissolved in 2 l methanol and are added dropwise into the mixture via a dropping funnel. After the addition it is stirred 120 min under reflux and subsequently cooled down and neutralized with aqueous phosphoric acid. The precipitated product is sucked off and dried. After analysis by HPLC a content of 92% N-monomethyl-N,N′,N″-tris(methoxycarbonyl)-melamine of the following formula (VI) is determined:

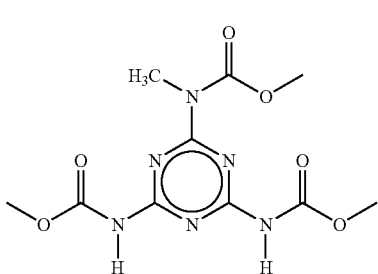

(VI)

Example 4

0.5 Mol product from example 1 (N,N′,N″-trimethyl-N,N′,N″-tris(methoxycarbonyl)-melamine) are heated to 100° C. in 12 molar equivalents 2-hydroxyethylacrylate in the presence of 1% zirconacetylacetonate and 0.5% hydrochinon-monomethylether and stirred for 5 h. Subsequently, the excess hydroxyethylacrylate is destilled off. The residue contains 68% of the desired final compound (VII).

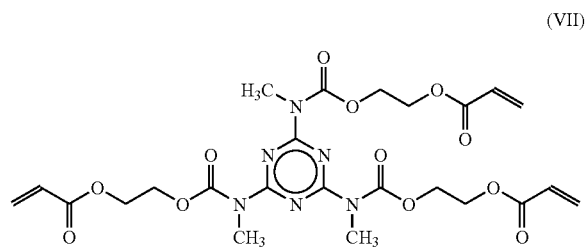

(VII)

Example 5

0.5 Mol product from example 2 (N,N,N',N''-tetramethyl-N',N''-bis(methoxycarbonyl)-melamine) are heated to 100° C. in 8 molar equivalents 2-hydroxyethylacrylate in the presence of 1% zirconacetylacetonate and 0.5% hydrochinon-monomethylether and stirred for 5 h. Subsequently, the excess hydroxyethylacrylate is destilled off. The residue contains 46% of the desired final compound (VIII).

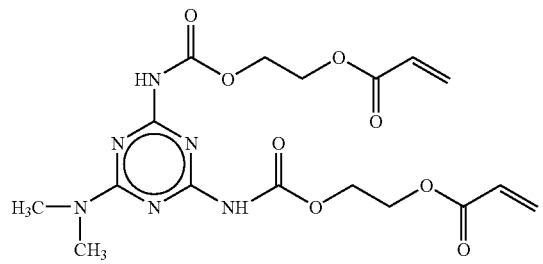

(VIII)

Example 6

In a three-neck round bottom flask (500 ml) with a gas feeding tube, inside thermometer, heatable dropping funnel and reflux cooler 100 ml chlorbenzene are flushed with nitrogen for 30 min and subsequently loaded with phosgene at 0° C. for 10 min. A solution of 1.51 g N,N,N',N''-tetramethylmelamine (8.28 mmol) in 100 ml chlorbenzene were added within 30 min, whereby the temperature increases to 25° C. In the presence of a weak phosgene stream through the mixture it was stirred 1 h at 25° C. and 1 h at 60° C. A suspension of N-methyl-N-triazinyl-carbamoylchloride was obtained.

At 130° C. nitrogen was flushed through the mixture for 15 min in order to drive out excessive solved phosgene. After cooling the mixture to 70° C. 100 ml 2-propanol (1.31 mol) were added within 15 min whereby the mixture cleared up. For completion of the reaction the mixture was stirred 1 h at 80° C. in an upright (upright maintained) nitrogen stream. After removing the solvent under reduced pressure ductile clear oil is obtained which solidifies after standing under reduced pressure in dry atmosphere.

Analyses by HPLC-MS, $^1$H-NMR, $^{13}$C-NMR, and ESI-MS (pos. mode) show that the product consisted of the desired carbamates 4-dimethylamino-6-(isopropoxycarbonyl-methyl-amino)-1,3,5-triazine-2-yl)-methyl-carbamine acid isopropylester (XII) and (4-dimethylamino-6-methylamino-1,3,5-triazine-2-yl)-methyl-carbamine acid isopropylester (X) and contained low amounts of the starting material N,N,N',N''-tetramethyl melamine (XI), (see table 1)

TABLE 1

Result of the product analysis of Example 6 by HPLC/MS

| Peak Nr. | [M + H]⁺ | Structural formulae | | Area-% |
|---|---|---|---|---|
| 1 | 269.06 | | (X) | 18.4% |
| 2 | 183.19 | | (XI) | 23.8% |
| 3 | 355.3 | | (XII) | 57.8% |

"Area-%" means thereby here and in the further examples the area in the HPLC-chromatogram allocated percentage-wise to the respective peak. [M + H]⁺ indicates in each case the determined mass of the substance contained in the peak plus the mass of a proton in g/mol.

Analysis Data for Peak No. 1:

$^1$H-NMR (200 MHz, CDCl$_3$): δ=6.88 (s$_b$, 1H, —NH), 5.10 (p, J=6.25 Hz, 1H, —CH—(CH$_3$)$_2$), 3.36 (s, 3H, >N—CH$_3$), 3.16 (s, 6H, —N(CH$_3$)$_2$), 2.97 (d, J=4.92 Hz, 3H, —NH(CH$_3$)), 1.32 (d, J=6.25 Hz, 6H, —CH—(CH$_3$)$_2$) ppm.

$^{13}$C-NMR (APT puts program, 50 MHz, CDCl$_3$): δ=164.7 (>C=O or =N—C=N—), 154.3 (>C=O or =N—C=N—), 164.7 (>C=O or =N—C=N—), 163.0 (>C=O or =N—C=N—), 158.8 (>C=O or =N—C=N—), 154.3 (>C=O or =N—C=N—), 70.88 (—CH(CH$_3$)$_2$), 36.53 (—N(CH$_3$)$_2$), 33.91 (>N—CH$_3$), 27.78 (—NH—CH$_3$), 22.18 (—CH(CH$_3$)$_2$) ppm.

ESI-MS (c~0.1 mg·cm$^{-3}$, CHCl$_3$:iPrOH=1:1, positive ion mode): m/z=269.13 [M+H]$^+$ TLC: R$_f$(ethyl acetate)=0.67

Analysis Data for Peak No. 3:

$^1$H-NMR (200 MHz, CDCl$_3$): δ=5.10 (p, J=6.26 Hz, 1H, —CH—(CH$_3$)$_2$), 3.42 (s, 3H, >N—CH$_3$ or —N(CH$_3$)$_2$), 3.20 (s, 3H, >N—CH$_3$ or —N(CH$_3$)$_2$), 1.33 (d, J=6.26 Hz, 6H, —CH—(CH$_3$)$_2$) ppm.

$^{13}$C-NMR (APT pulsprogram, 50 MHz, CDCl$_3$): δ=161.1 (>C=O or =N—C=N—), 154.6 (>C=O or =N—C=N—), 154.4 (>C=O or =N—C=N—), 74.40 (—CH(CH$_3$)$_2$), 38.38 (>N—CH$_3$ or —N(CH$_3$)$_2$), 33.61 (>N—CH$_3$ or —N(CH$_3$)$_2$), 21.90 (—CH(CH$_3$)$_2$) ppm.

ESI-MS (c~0.1 mg·cm$^{-3}$, CHCl$_3$:iPrOH=1:1, positive ion mode): m/z=355.13 [M+H]$^+$ TLC: R$_f$(ethyl acetate)=0.82

Example 7

In a three-neck round bottom flask (500 ml) with gas feeding tube, inside thermometer, heatable dropping funnel and reflux cooler 100 ml chlorbenzene are flushed 30 min with nitrogen and loaded afterwards with phosgene for 10 min at 0° C. A solution of 1.26 g N,N',N"-trimethylmelamine (7.48 mmol) in 100 ml chlorbenzene are added dropwise in 30 min whereby the temperature increases to 20° C. It was stirred 1 h at 20° C. and 1 h at 60° C. in the presence of a weak phosgene stream through the mixture. A suspension of N-methyl-N-triazinyl-carbamoylchloride was obtained.

At 130° C. nitrogen was flushed through the mixture for 15 min in order to drive out excessive solved phosgene. After cooling the mixture to 70° C. 100 ml 2-propanol (1.31 mol) were added in 15 min whereby the mixture became clear. For completing the reaction the mixture was stirred 1 h at 80° C. under an upright nitrogen stream. After removing the solvent under reduced pressure a ductile clear oil was obtained which solidified after standing under reduced pressure in dry atmosphere.

Analysis by HPLC-MS show (compare table 2) that the product consisted of the desired carbamate [4,6-bis-(methylamino)-1.3.5-triazine-2-yl]-methyl-carbamine acid-isopropylester (XIII) [4-(isopropoxycarbonyl-methylamino)-6-methylamino-1.3.5-triazine-2-yl]-methyl-carbamine acid-isopropylester (XV) and [4,6-bis-(isopropoxycarbonyl-methylamino)-1.3.5-triazine-2-yl]-methyl-carbamine acid-isopropylester (XVI) and contained low amounts of the starting material N,N',N"-trimethylmelamine (XIV) and of polynuclear melamine derivatives (side products).

TABLE 2

Result of the product analysis of Example 7 by HPLC/MS

| Peak Nr. | [M + H]$^+$ | Structural formulae | | Area-% |
|---|---|---|---|---|
| 1 | 255.16 | | (XIII) | 17.3 |
| 2 | 169.12 | | (XIV) | 13.6 |
| 3 | 341.19 | | (XV) | 22.8 |

TABLE 2-continued

Result of the product analysis of Example 7 by HPLC/MS

| Peak Nr. | [M + H]+ | Structural formulae | | Area-% |
|---|---|---|---|---|
| 4 | 427.23 | (triazine with three isopropyl carbamate groups, each N-methyl) | (XVI) | 46.3 |

Example 8

In a three-neck round bottom flask (500 ml) with gas feeding tube, inside thermometer, heatable dropping funnel and reflux cooler 100 ml chlorbenzene are flushed with nitrogen for 30 min and afterwards loaded with phosgene for 10 min at 0° C. A solution of 1.25 g N,N',N''-trimethyl melamine (7.43 mmol) in 100 ml chlorbenzene was added dropwise in 30 min whereby the temperature increases to 20° C. The mixture was stirred 1 h at 20° C. and 1 h at 60° C. in the presence of a weak phosgene stream. A suspension of N-methyl-N-triazinyl-carbamoylchloride was obtained.

At 130° C. nitrogen was flushed through the mixture for 15 min in order to drive out excessive solved phosgene. After cooling the mixture to 80° C. 3.33 g phenol (35.4 mmol) were added in 15 min whereby the mixture became clear. For completion of the reaction the mixture was stirred 1 h under an upright nitrogen stream. After removing the solvent under reduced pressure a high viscous brown oil was obtained which contained the desired carbamate (compare table 3) according to analysis by HPLC.

TABLE 3

Result of the product analysis of Example 8 by HPLC/MS

| Peak Nr. | [M + H]+ | Structural formulae | Area-% |
|---|---|---|---|
| 1 | 289.14 | (triazine with HN-methyl, N-methyl-N-phenylcarbamate, and NH-methyl groups) | 17.4 |
| 2 | 169.12 | (N,N',N''-trimethyl melamine) | 12.0 |
| 3 | 409.16 | (triazine with HN-methyl and two N-methyl-N-phenylcarbamate groups) | 20.7 |

TABLE 3-continued

Result of the product analysis of Example 8 by HPLC/MS

| Peak Nr. | [M + H]⁺ | Structural formulae | Area-% |
|---|---|---|---|
| 4 | 529.18 | (triazine with three N-methyl-N-phenoxycarbonyl groups) | 49.9 |

Example 9

In a three-neck round bottom flask (500 ml) with gas feeding tube, inside thermometer, heatable dropping funnel and reflux cooler 100 ml chlorbenzene were flushed with nitrogen for 30 min and afterwards loaded with phosgene for 10 min at 0° C. A solution of 1.25 g N,N',N''-trimethyl melamine (7.43 mmol) in 100 ml chlorbenzene was added dropwise in 30 min whereby the temperature increases to 20° C. The mixture was stirred 1 h at 20° C. and 1 h at 60° C. in the presence of a weak phosgene stream. A suspension of the N-methyl-N-triazinyl-carbamoylchloride was obtained.

At 130° C. nitrogen was flushed through the mixture for 15 min for driving out excessive solved phosgene. After cooling the mixture to 60° C. 1.42 g methanol (44.4 mmol) were added in 15 min whereby the mixture became clear. For completing the reaction the mixture was stirred 1 h at 60° C. under an upright nitrogen stream. After removing the solvent under reduced pressure ductile clear oil was obtained which solidified after standing under reduced pressure in dry atmosphere and which contained the desired carbamates according to the analysis by HPLC/MS (compare table 4).

TABLE 4

Result of the product analysis of Example 9 by HPLC/MS

| Peak Nr. | [M + H]⁺ | Structural formulae | Area-% |
|---|---|---|---|
| 1 | 227.13 | (triazine with HN-Me, N(Me)-C(O)OMe, NHMe) | 17.2 |
| 2 | 169.12 | (N,N',N''-trimethyl melamine) | 9.2 |
| 3 | 285.13 | (triazine with HN-Me, two N(Me)-C(O)OMe) | 23.5 |

TABLE 4-continued

Result of the product analysis of Example 9 by HPLC/MS

| Peak Nr. | [M + H]+ | Structural formulae | Area-% |
|---|---|---|---|
| 4 | 343.14 | | 47.1 |

Example 10

In a three-neck round bottom flask (500 ml) with gas feeding tube, inside thermometer, heatable dropping funnel and reflux cooler 100 ml chlorbenzene were flushed with nitrogen for 30 min and afterwards loaded with phosgene for 10 min at 0° C. A solution of 1.5 g N,N,N',N''-tetramethyl melamine (8.23 mmol) in 100 ml chlorbenzene were added dropwise in 30 min whereby the temperature increases to 20° C. The mixture was stirred 1 h at 20° C. and 1 h at 60° C. under a weak phosgene stream through the mixture. A suspension of the N-methyl-N-triazinyl-carbamoylchloride was obtained.

At 130° C. nitrogen was flushed through the mixture for 15 min in order to drive out excessive solved phosgene. After cooling the mixture to 60° C. 1.58 g methanol (49.4 mmol) were added in 15 min whereby the mixture became clear. For completing the reaction the mixture was stirred 1 h at 60° C. under an upright nitrogen stream. After removing the solvent under reduced pressure ductile clear oil was obtained which solidified after standing under reduced pressure in dry atmosphere and which contains the desired carbamate according to the analysis by HPLC/MS (compare table 5).

TABLE 5

Result of the products analysis of Example 10 by HPLC/MS

| Peak Nr. | [M + H]+ | Structural formulae | Area-% |
|---|---|---|---|
| 1 | 241.14 | | 30.3 |
| 2 | 183.14 | | 13.8 |
| 3 | 299.15 | | 55.9 |

Example 11

In a three-neck round bottom flask (500 ml) with gas feeding tube, inside thermometer, heatable dropping funnel and reflux cooler 100 ml chlorbenzene were flushed with nitrogen for 30 min and loaded afterwards with phosgene for 10 min at 0° C. A solution of 1.25 g N,N',N''-trimethylmelamine (7.43 mmol) in 100 ml chlorbenzene was added dropwise in 30 min whereby the temperature increases to 20° C. the mixture was stirred 1 h at 20° C. and 1 h at 60° C. under a weak phosgene stream. A suspension of the N-methyl-N-triazinyl-carbamoylchloride was obtained.

At 130° C. nitrogen was flushed through the mixture for 15 min in order to drive out excessive solved phosgene. After cooling the mixture to 60° C. 4.41 g 1-octanol (33.88 mmol) were added in 15 min whereby the mixture became clear. For completing the reaction the mixture was stirred 1 h at 60° C. under an upright nitrogen stream. After removing the solvent under reduced pressure and the volatile ingredients ductile oil was obtained which contains the desired carbamate according to analysis by HPLC/MS (compare table 6).

TABLE 6

Result of the products analysis of Example 11 by HPLC/MS

| Peak Nr. | [M + H]⁺ | Structural formulae | Area-% |
|---|---|---|---|
| 1 | 325.24 | 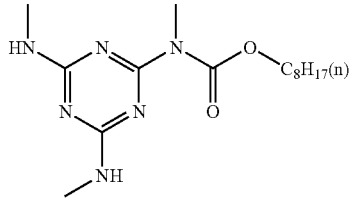 | 14.2 |
| 2 | 169.12 | 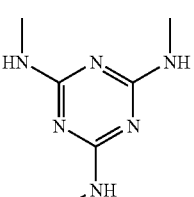 | 19.2 |
| 3 | 481.35 | 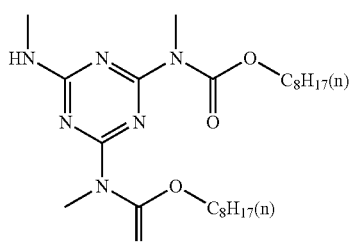 | 19.5 |
| 4 | 637.47 | 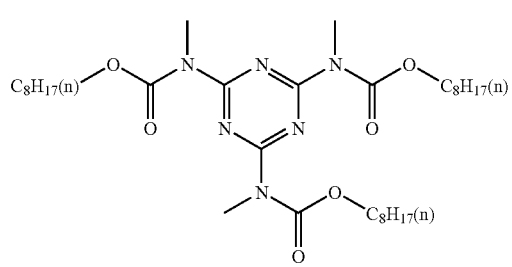 | 44.1 |

The designation $C_8H_{17}(n)$ used in the structural formulas of table 6 means thereby that in each case it is a matter of a n-octyl moiety (thus a linear octyl moiety).

Example 12

In a three-neck round bottom flask (500 ml) with gas feeding tube, inside thermometer, heatable dropping funnel and reflux cooler 100 ml nitrobenzene are flushed with nitrogen for 30 min and loaded afterwards with phosgene for 10 min at 0° C. A solution of 1.25 g N,N',N''-trimethylmelamine (7.43 mmol) in 100 ml nitrobenzene were added dropwise in 30 min whereby the temperature increases to 20° C. The mixture was stirred 1 h at 20° C. and 1 h at 60° C. under a weak phosgene stream. A suspension of the N-methyl-N-triazinyl-carbamoylchloride was obtained.

At 130° C. nitrogen was flushed through the mixture for 15 min in order to drive out excessive solved phosgene. After cooling the mixture to 60° C. 5.95 g (2-hydroxyethyl)-methacrylate (45.7 mmol; stabilized with 0.3% 2,2,6,6-tetramethyl-piperidin-1-oxyl (TEMPO)) were added in 15 min whereby the mixture became clear. For completing the reaction the mixture was stirred 1 h at 60° C. under an upright nitrogen stream. After removing the solvent and the volatile ingredients under reduced pressure a dark oil was obtained which contained the desired carbamates according to analysis by HPLC/MS (compare table 7).

TABLE 7

Result of the products analysis of Example 12 by HPLC/MS

| Peak Nr. | [M + H]+ | Strukturformel | Area-% |
|---|---|---|---|
| 1 | 325 | 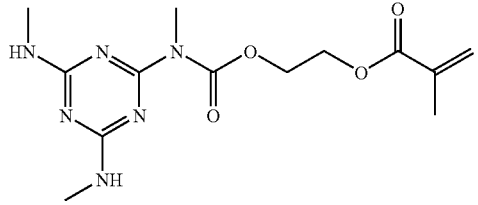 [SMILES: C=C(C)C(=O)OCCOC(=O)N(C)c1nc(NC)nc(NC)n1] | 16.7 |
| 2 | 169.12 | 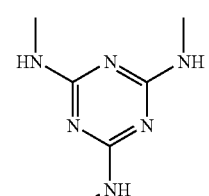 | 16.8 |
| 3 | 481 | 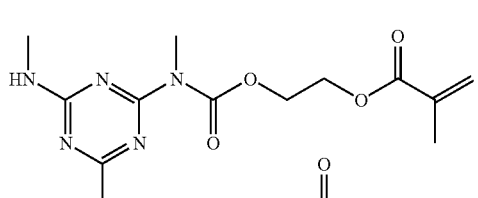 | 21.3 |
| 4 | 637 | 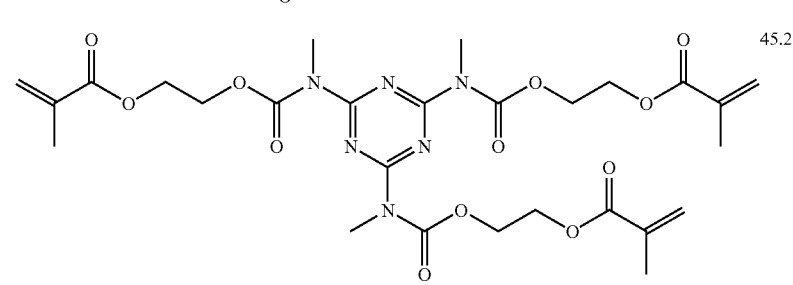 | 45.2 |

The respective reaction products of the above-mentioned examples can further be converted in analogy to the examples 4 and 5. Thereby, the reaction products can be separated from each other and purified before a further conversion or also can be further converted without a prior processing.

The invention claimed is:

1. Triazine derivatives according to the general formula (Ia)

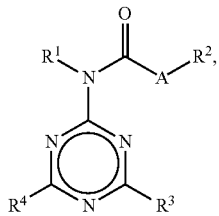

wherein $R^3$ means $Q^1$ or a moiety of the formula $R^5$—N—$R^6$ connected with the nitrogen atom to the triazine ring of the structure of formula (I), wherein $Q^1$ means a linear or branched $C_1$-$C_{50}$-alkyl or a cyclic substituent in the form of a $C_5$-$C_{20}$-cycloalkyl, a $C_5$-$C_{20}$-aryl, a $C_1$-$C_{20}$-alkyl substituted $C_5$-$C_{20}$-aryl, a $C_2$-$C_{20}$-alkenyl substituted $C_5$-$C_{20}$-aryl or of an imide of a cyclic saturated or unsaturated carboxylic acid, wherein the $C_1$-$C_{50}$-alkyl or the cyclic substituent can be interrupted by one or multiple oxygen atoms, sulphur atoms, substituted and/or unsubstituted nitrogen atoms and/or by one or multiple groups of the type —C(O)O—, —OC(O)—, —C(O)—, —NHC(O)O—, —OC(O)NH— and/or —OC(O)O—, $R^4$ means a moiety of the formula $R^7$—N—$R^8$ connected with the nitrogen atom to the triazine ring of the structure of the formula (Ia), $R^1$, $R^5$, and $R^7$ mean independently from each other H or $Q^2$, wherein $Q^2$ means in each case a linear or branched $C_1$-$C_{50}$-alkyl, $C_5$-$C_{20}$-cycloalkyl, $C_5$-$C_{20}$-aryl, $C_1$-$C_{20}$-alkyl substituted $C_5$-$C_{20}$-aryl, $C_2$-$C_{20}$-alkenyl or $C_2$-$C_{20}$-alkenyl substituted $C_5$-$C_{20}$-aryl, that in each case can be interrupted by one or multiple oxygen atoms, sulphur atoms, substituted and/or unsubstituted nitrogen atoms and/or by one or multiple groups of the type —C(O)O—, —OC(O)—, —C(O)—, —NHC(O)O—, —OC(O)NH— and/or —OC(O)O—, A means —$NR^2$—, —$NR^{62}$— or —$NR^{82}$—, $R^6$ means H, $Q^2$-CO-A-$R^2$, —CO-A-$R^{61}$, $R^8$ means —CO-A-$R^2$, —CO-A-$R^{61}$ or —CO-A-$R^{81}$ $R^2$, $R^{61}$, $R^{62}$, $R^{81}$ and $R^{82}$ mean independent from each other $Q^2$, a moiety of a substituted or non-substituted alcohol, a moiety of a substituted or unsubstituted polyvalent alcohol, a moiety of an amine, a moiety of an amino alcohol, a moiety of a diamine or a moiety of the general formula (II)

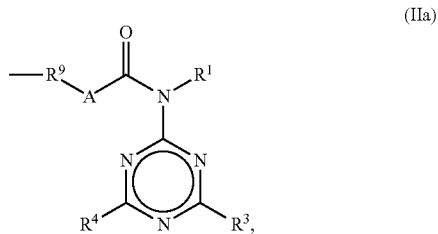

(IIa)

whereby $R^9$ means $Q^2$, with the stipulation that in case $R^3$ means $R^5$—N—$R^6$ and $R^4$ means $R^7$—N—$R^8$, at least one of the moieties $R^1$, $R^5$, and $R^7$ means $Q^2$ and is bound to a nitrogen atom that is covalently connected to the moiety —CO-A-$R^2$, —CO-A-$R^{61}$ or —CO-A-$R^{81}$, or at least the moieties $R^5$ and $R^6$ on the one hand and the moieties $R^7$ and $R^8$ on the other hand mean in each case $Q^2$ or mixtures thereof.

2. Triazine derivatives according to claim 1, wherein the moieties $R^2$, $R^{61}$, $R^{62}$, $R^{81}$ and $R^{82}$ are identical.

3. Triazine derivatives according to claim 1, wherein they have at least one of an adjustable viscosity or an adjustable melting behaviour or an adjustable compatibility to other compounds.

4. Triazine derivatives according to claim 1, wherein at least one of the moieties $R^1$, $R^5$, $R^6$, $R^7$ and $R^8$ mean $Q^2$ independently of the meaning of the moieties $R^3$ and $R^4$.

5. Triazine derivatives according to claim 1, wherein at least one of the moieties $R^1$, $R^5$, $R^6$, $R^7$ and $R^8$ mean $Q^2$ independently of the meaning of the moieties $R^3$ and $R^4$ and are bound to a nitrogen atom which is covalently linked to the moiety —CO-A-$R^2$, —CO-A-$R^{61}$ or —CO-A-$R^{81}$.

6. Triazine derivatives according to claim 1, wherein at least one of the moieties $R^5$, $R^6$, $R^7$ and $R^8$ mean $Q^2$ independently of the meaning of the moieties $R^3$ and $R^4$.

7. Triazine derivatives according to claim 1, wherein the cyclic substituent has a nitrogen atom as part of the cyclic structure via which it is bound to the triazine ring of the structure of the formula (Ia).

8. Triazine derivatives according to claim 1, wherein each of the nitrogen atoms bound to the triazine ring of the structure of the formula (I) (Ia) is substituted in the same manner so that structural symmetrical triazine derivatives are provided.

9. Triazine derivatives according to claim 1, wherein $R^2$, $R^{61}$, $R^{62}$, $R^{81}$ and $R^{82}$ are independently from each other a moiety of methanol, ethanol, propanol, isopropanol, butanol, isobutanol, pentanol, hexanol, benzylalcohol, phenol, ethylenglycolmonomethylether, ethylhexylalcohol, dodecylalcohol and/or stearylalcohol.

10. Triazine derivatives according to claim 1, wherein $R^2$, $R^{61}$, $R^{62}$, $R^{81}$ and $R^{82}$ are independently from each other a moiety of the compound 2-hydroxyethylacrylate, 2-hydroxypropylacrylate, 4-hydroxybutylacrylate, 6-hydroxyhexylacrylate, diethylenglycolmonoacrylate, triethylenglycolmonoacrylate, dipropylenglycol-monoacrylate, tripropylenglycol-monoacrylate, trimethylolpropandiacrylate, pentaerythrit-diacrylate, pentaerythrittriacrylate, 2-hydroxyethylmethacrylate, 2-hydroxypropylmeth-acrylate, 4-hydroxybutylmethacrylate, 6-hydroxyhexylmethacrylate, diethylenglycol-monomethacrylate, triethylenglycol-monomethacrylate, dipropylenglycolmonometh-acrylate, tripropylenglycol-monomethacrylate, trimethylolpropan-dimethacrylate, penta-erythritdimethacrylate, penta-erythrittrimethacrylate and/or 4-hydroxybutylvinylether.

11. Triazine derivatives according to claim 1, wherein $R^2$, $R^{61}$, $R^{62}$, $R^{81}$ and $R^{82}$ are independently from each other a moiety of ethylenglycol, butandiol, neopentylglycol, hexandiol, octandiol, dodecandiol, octadecandiol, glycol, trimethylolpropane, pentaerythrit, of polyethylenglycoles with molar masses of 200 to 5000, of polypropylenglycoles with molar masses of 200 to 5000, of polytetrahydrofuranes with molar masses of 200 to 5000 and/or of polyesterdioles on the basis of saturated dicarboxylic acids like terephthalic acid, isophthalic acid, naphthalindicarboxylic acid, maleinic acid, fumaric acid and/or itakonic acid.

12. Triazine derivatives according to claim 1, wherein $R^2$, $R^{61}$, $R^{62}$, $R^{81}$ and $R^{82}$ are independently from each other a moiety of ethylamine, diethylamine, propylamine, dipropylamine, isopropylamine, diisopropylamine, butylamine, dibutylamine, hexylamine, hexamethylendiamine, propylendiamine, butylendiamine and/or ethylendiamine.

13. Triazine derivatives according to claim 1, wherein $R^2$, $R^{61}$, $R^{62}$, $R^{81}$ and $R^{82}$ are independently from each other a moiety of aminoethanol, aminopropanol, aminoethoxyethanol, diethanolamine, triethanolamine, triisopropanol-amine, diisopropanolamine and/or isopropanolamine.

14. Triazine derivatives according to claim 1, wherein at least one en of the moieties $R^1$, $R^5$, $R^6$, $R^7$ and $R^8$ have a $C_1$-$C_{18}$-alkyl group.

15. Triazine derivatives according to claim 1, wherein the moiety $R^6$ or the moiety $R^8$ or both have only the meaning of $Q^2$, but not the meaning of CO-A-$R^2$, —CO-A-$R^{61}$ or —CO-A-$R^{81}$.

16. Triazine derivatives according to claim 1, wherein the triazine derivatives are polymerizable by radiation.

17. Triazine derivatives according to claim 16, wherein the radiation is electromagnetical radiation or particle radiation.

18. Triazine derivatives according to claim 1, wherein the triazine derivatives are polymerizable chemically or thermally or both.

19. Triazine derivatives according to claim 1, wherein the triazine derivatives are polymerizable by polycondensation or polyaddition.

20. Triazine derivatives according to claim 1, wherein the triazine derivatives are present as oligomers or polymers or both.

21. Triazine derivatives according to claim 20, wherein at least two triazine derivative monomers are connected to each other via polyvalent alcohols, amines or amino alcohols.

22. A composition, comprising triazine derivatives according to claim 1 with at least one urea resin, urea-melamine resin, melamine resin, melamine-phenol-resin, phenol resin, polyester, polyacrylate, polyurethane, epoxide, polyether, or mixture thereof.

23. Triazine derivatives according to claim 1, wherein the triazine derivatives are present as oligomers or polymers or both.

24. Triazine derivatives according to claim 23, wherein at least two triazine derivative monomers are connected to each other via polyvalent alcohols, amines or amino alcohols.

25. A method for the production of triazine derivatives of general formula (I),

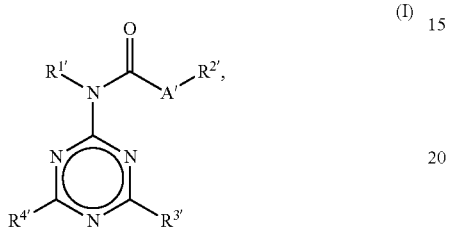

(I)

wherein
- $R^{3'}$ means $Q^1$ or a moiety of the formula $R^{5'}$—N—$R^{6'}$ connected with the nitrogen atom to the triazine ring of the structure of formula (I), wherein
  - $Q^1$ means a linear or branched $C_1$-$C_{50}$-alkyl or a cyclic substituent in the form of a $C_5$-$C_{20}$-cycloalkyl, a $C_5$-$C_{20}$-aryl, a $C_1$-$C_{20}$-alkyl substituted $C_5$-$C_{20}$-aryl, a $C_2$-$C_{20}$-alkenyl substituted $C_5$-$C_{20}$-aryl or of an imide of a cyclic saturated or unsaturated carboxylic acid, wherein the $C_1$-$C_{50}$-alkyl or the cyclic substituent can be interrupted by one or multiple oxygen atoms, sulphur atoms, substituted and/or unsubstituted nitrogen atoms and/or by one or multiple groups of the type —C(O)O—, —OC(O)—, —C(O)—, —NHC(O)O—, —OC(O)NH— and/or —OC(O)O—,
- $R^{4'}$ means $Q^1$ or a moiety of the formula $R^{7'}$—N—$R^{8'}$ connected with the nitrogen atom to the triazine ring of the structure of the formula (I),
- $R^{1'}$, $R^{5'}$, and $R^{7'}$ mean independently from each other H or $Q^2$, wherein
  - $Q^2$ means in each case a linear or branched $C_1$-$C_{50}$-alkyl, $C_5$-$C_{20}$-cycloalkyl, $C_5$-$C_{20}$-aryl, $C_1$-$C_{20}$-alkyl substituted $C_5$-$C_{20}$-aryl, $C_2$-$C_{20}$-alkenyl or $C_2$-$C_{20}$-alkenyl substituted $C_5$-$C_{20}$-aryl, that in each case can be interrupted by one or multiple oxygen atoms, sulphur atoms, substituted and/or unsubstituted nitrogen atoms and/or by one or multiple groups of the type —C(O)O—, —OC(O)—, —C(O)—, —NHC(O)O—, —OC(O)NH— and/or —OC(O)O—,
- A' means —O—, —NH—, —$NR^{2'}$—, —$NR^{62'}$— or —$NR^{82'}$—,
- $R^{6'}$ and $R^{8'}$ mean independent from each other means H, $Q^2$-CO-A-$R^{2'}$, —CO-A-$R^{61'}$, —CO-A-$R^{81'}$,
- $R^{2'}$, $R^{61'}$, $R^{62'}$, $R^{81'}$ and $R^{82'}$ mean independent from each other $Q^2$, a moiety of a substituted or non-substituted alcohol, a moiety of a substituted or unsubstituted polyvalent alcohol, a moiety of an amine, moiety of an amino alcohol, a moiety of a diamine or a moiety of the general formula (II),

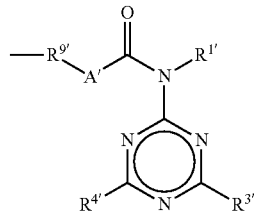

(II)

whereby $R^{9'}$ means $Q^2$,
with the stipulation that in case $R^{3'}$ means $R^{5'}$—N—$R^{6'}$ and $R^{4'}$ means $R^{7'}$—N—$R^{8'}$,
- at least one of the moieties $R^{1'}$, $R^{5'}$, and $R^{7'}$ means $Q^2$ and is bound to a nitrogen atom that is covalently connected to the moiety —CO-A-$R^{2'}$, —CO-A-$R^{61'}$ or —CO-A-$R^{81'}$, or
- at least the moieties $R^{5'}$ and $R^{6'}$ on the one hand and the moieties $R^{7'}$ and $R^{8'}$ on the other hand mean in each case $Q^2$ or
- at least one of the moieties $R^{5'}$ or $R^{6'}$ means $Q^2$ and $R^{7'}$ and $R^{8'}$ mean both simultaneously H, or mixtures thereof, comprising the steps of:

A) converting a triazine derivative according to the general formula (IX)

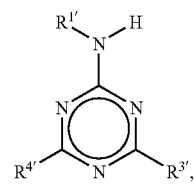

(IX)

whereby
- $R^{3'}$ means $Q^1$ or a moiety of the formula $R^{5'}$—N—$R^{6'}$ bound with its central nitrogen atom to the triazine ring of the structure of the formula (IX), wherein
  - $Q^1$ means a linear or branched $C_1$-$C_{50}$-alkyl or a cyclic substituent in the form of a $C_5$-$C_{20}$-cycloalkyl, a $C_5$-$C_{20}$-aryl, a $C_1$-$C_{20}$-alkyl substituted $C_5$-$C_{20}$-aryl, a $C_2$-$C_{20}$-alkenyl substituted $C_5$-$C_{20}$-aryl or an imide of cyclic saturated or unsaturated carboxylic acids, wherein the $C_1$-$C_{50}$-alkyl or the cyclic substituent can be interrupted by one or multiple oxygen atoms, sulphur atoms, substituted and/or unsubstituted nitrogen atoms and/or by one or multiple groups of the type —C(O)O—, —OC(O)—, —C(O)—, —NHC(O)O—, —OC(O)NH— and/or —OC(O)O—,
- $R^{4'}$ means $Q^1$ or a moiety of the formula $R^{7'}$—N—$R^{8'}$ bound with the nitrogen atom to the triazine ring of the structure of the formula (IX),
- $R^{1'}$, $R^{5'}$, and $R^{7'}$ independently from each other mean H or $Q^2$, wherein
  - $Q^2$ means in each case linear or branched $C_1$-$C_{50}$-alkyl, $C_5$-$C_{20}$-cycloalkyl, $C_5$-$C_{20}$-aryl, $C_1$-$C_{20}$-alkyl substituted $C_5$-$C_{20}$-aryl, $C_2$-$C_{20}$-alkenyl or $C_2$-$C_{20}$-alkenyl substituted $C_5$-$C_{20}$-aryl, which can be interrupted in each case by one or multiple oxygen atoms, sulphur atoms, substituted and/or unsubstituted nitrogen atoms and/or by one or multiple groups of the type —C(O)O—, —OC(O)—, —C(O)—, —NHC(O)O—, —OC(O)NH— and/or —OC(O)O—, $R^{6'}$ and $R^{8'}$ mean independently from each other H, $Q^2$, —CO-A-$R^{61'}$ or —CO-A-$R^{81'}$, A' means —O—, —NH— —CO-A-$R^{62'}$ or —CO-A-$R^{82'}$, $R^{61'}$, $R^{62'}$, $R^{81'}$ and $R^{82'}$ mean independently from each other $Q^2$, a moiety of a substituted or unsubstituted alcohol, a moiety of the substituted or unsubstituted polyvalent alcohol, a moiety of an amine, a moiety of an amino alcohol, a moiety of a diamine or a moiety of the general formula (II),

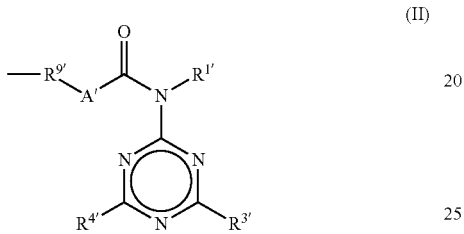

(II)

Whereby $R^{9'}$ means $Q^2$,
with phosgen and

B) converting the carbamoylchloride of the triazine derivative formed in step A) with a substituted or unsubstituted alcohol of the general formula $R^{2'}$—OH, a substituted or unsubstituted polyvalent alcohol of the general formula $R^{2'}$-$(OH)_n$ with n≥2, an amine of the general formula $R^{2'}$—$NH_2$ or $R^{2'}$—NH—$R^{20'}$, an amino alcohol of the general formula OH—$R^{2'}$—$NH_2$ or $R^{2'}$—NH—$R^{20'}$—OH, a diamine of the general formula $R^{2'}$, —$(NH_2)_2$ or a moiety of the general formula (II),
whereby $R^{2'}$ and $R^{20'}$ mean independently from each other $Q^2$, a moiety of a substituted or unsubstituted alcohol, a moiety of a substituted or unsubstituted polyvalent alcohol, a moiety of an amine, a moiety of an amino alcohol, a moiety of a diamine or a moiety of the general formula (II).

26. Triazine derivatives according to the general formula (Ib)

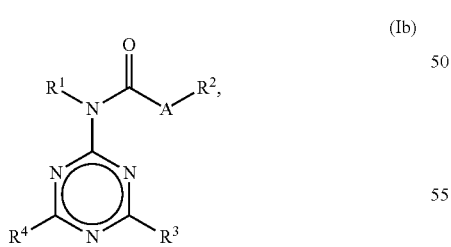

(Ib)

wherein
$R^3$ means $Q^1$ or a moiety of the formula $R^5$—N—$R^6$ connected with the nitrogen atom to the triazine ring of the structure of formula (Ib), wherein
$Q^1$ means a linear or branched $C_1$-$C_{50}$-alkyl or a cyclic substituent in the form of a $C_5$-$C_{20}$-cycloalkyl, a $C_5$-$C_{20}$-aryl, a $C_1$-$C_{20}$-alkyl substituted $C_5$-$C_{20}$-aryl, a $C_2$-$C_{20}$-alkenyl substituted $C_5$-$C_{20}$-aryl or of an imide of a cyclic saturated or unsaturated carboxylic acid, wherein the $C_1$-$C_{50}$-alkyl or the cyclic substituent can be interrupted by one or multiple oxygen atoms, sulphur atoms, substituted and/or unsubstituted nitrogen atoms and/or by one or multiple groups of the type —C(O)O—, —OC(O)—, —C(O)—, —NHC(O)O—, —OC(O)NH— and/or —OC(O)O—, $R^4$ means $Q^1$ or a moiety of the formula $R^7$—N—$R^8$ connected with the nitrogen atom to the triazine ring of the structure of the formula (Ib), $R^1$, $R^5$, and $R^7$ mean independently from each other H or $Q^2$, wherein
$Q^2$ means in each case a linear or branched $C_1$-$C_{50}$-alkyl, $C_5$-$C_{20}$-cycloalkyl, $C_5$-$C_{20}$-aryl, $C_1$-$C_{20}$-alkyl substituted $C_5$-$C_{20}$-aryl, $C_2$-$C_{20}$-alkenyl or $C_2$-$C_{20}$-alkenyl substituted $C_5$-$C_{20}$-aryl, that in each case can be interrupted by one or multiple oxygen atoms, sulphur atoms, substituted and/or unsubstituted nitrogen atoms and/or by one or multiple groups of the type —C(O)O—, —OC(O)—, —C(O)—, —NHC(O)O—, —OC(O)NH— and/or —OC(O)O—, A means —O—, $R^6$ and $R^8$ mean independent from each other H, $Q^2$-CO-A-$R^2$, —CO-A-$R^{61}$, —CO-A-$R^{81}$, $R^2$, $R^{61}$, $R^{62}$, $R^{81}$ and $R^{82}$ mean independent from each other a moiety of a substituted or non-substituted alcohol selected from the compounds 2-hydroxyethylacrylate, 2-hydroxypropylacrylate, 4-hydroxybutylacrylate, 6-hydroxyhexyl-acrylate, diethylenglycolmonoacrylate, triethylenglycolmonoacrylate, dipropylenglycol-mono acrylate, tripropylenglycol-monoacrylate, trimethylolpropandiacrylate, pentaerythrit-diacrylate, pentaerythrittriacrylate, 2-hydroxyethylmethacrylate, 2-hydroxypropylmethacrylate, 4-hydroxybutylmethacrylate, 6-hydroxyhexylmethacrylate, diethylenglycolmonomethacrylate, triethylenglycol-monomethacrylate, dipropylenglycolmonometh-acrylate, tripropylenglycol-monomethacrylate, trimethylolpropandimethacrylate, penta-erythrit-dimethacrylate, penta-erythrittrimethacrylate and/or 4-hydroxybutylvinylether or a moiety of the general formula (II),

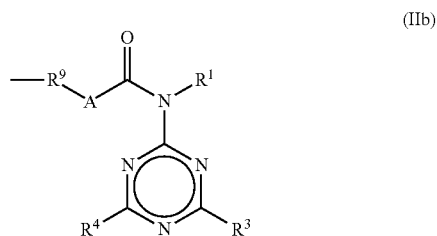

(IIb)

whereby $R^9$ means $Q^2$,
with the stipulation that in case $R^3$ means $R^5$—N—$R^6$ and $R^4$ means $R^7$—N—$R^8$,
at least one of the moieties $R^1$, $R^5$, and $R^7$ means $Q^2$ and is bound to a nitrogen atom that is covalently connected to the moiety —CO-A-$R^2$, —CO-A-$R^{61}$ or —CO-A-$R^{81}$, or
at least the moieties $R^5$ and $R^6$ on the one hand and the moieties $R^7$ and $R^8$ on the other hand mean in each case $Q^2$ or at least one of the moieties $R^5$ or $R^6$ means $Q^2$ and $R^7$ and $R^8$ mean both simultaneously H, or mixtures thereof.

27. Triazine derivatives according to claim 26, wherein they have at least one of an adjustable viscosity or an adjustable melting behaviour or an adjustable compatibility to other compounds.

28. Triazine derivatives according to claim 26, wherein at least one of the moieties $R^1$, $R^5$, $R^6$, $R^7$ and $R^8$ mean $Q^2$ independently of the meaning of the moieties $R^3$ and $R^4$.

29. Triazine derivatives according to claim 26, wherein at least one of the moieties $R^1$, $R^5$, $R^6$, $R^7$ and $R^8$ mean $Q^2$ independently of the meaning of the moieties $R^3$ and $R^4$ and are bound to a nitrogen atom which is covalently linked to the moiety —CO-A-$R^2$, —CO-A-$R^{61}$ or —CO-A-$R^{81}$.

30. Triazine derivatives according to claim 26, wherein at least one of the moieties $R^5$, $R^6$, $R^7$ and $R^8$ mean $Q^2$ independently of the meaning of the moieties $R^3$ and $R^4$.

31. Triazine derivatives according to claim 26, wherein the cyclic substituent has a nitrogen atom as part of the cyclic structure via which it is bound to the triazine ring of the structure of the formula (Ib).

32. Triazine derivatives according to claim 26, wherein each of the nitrogen atoms bound to the triazine ring of the structure of the formula (Ib) is substituted in the same manner so that structural symmetrical triazine derivatives are provided.

33. Triazine derivatives according to claim 26, wherein at least one of the moieties $R^1$, $R^5$, $R^6$, $R^7$ and $R^8$ have a $C_1$-$C_{18}$-alkyl group.

34. Triazine derivatives according to claim 26, wherein the moiety $R^6$ or the moiety $R^8$ or both have only the meaning of $Q^2$, but not the meaning of CO-A-$R^2$, —CO-A-$R^{61}$ or —CO-A-$R^{81}$.

35. Triazine derivatives according to claim 26, wherein the triazine derivatives are polymerizable by radiation.

36. Triazine derivatives according to claim 35, wherein the radiation is electromagnetical radiation or particle radiation.

37. Triazine derivatives according to claim 26, wherein the triazine derivatives are polymerizable chemically or thermally or both.

38. Triazine derivatives according to claim 26, wherein the triazine derivatives are polymerizable by polycondensation or polyaddition.

* * * * *

UNITED STATES PATENT AND TRADEMARK OFFICE
CERTIFICATE OF CORRECTION

| | | |
|---|---|---|
| PATENT NO. | : 8,569,423 B2 | Page 1 of 1 |
| APPLICATION NO. | : 12/599243 | |
| DATED | : October 29, 2013 | |
| INVENTOR(S) | : Rene Dicke et al. | |

It is certified that error appears in the above-identified patent and that said Letters Patent is hereby corrected as shown below:

On the Title Page, Item (75) Inventors, delete "Andreas Endersfelder," and insert -- Andreas Endesfelder, --

On the Title Page, Item (30), Column 1, insert -- Foreign Application Priority Data
May 31, 2007   (DE) .............................. 10 2007 025 451.4 --

In the Claims

Column 25, Line 6, Claim 1, after "A means" insert -- -NH-, --

Column 25, Line 62, Claim 8, after "formula" delete "(I)"

Column 26, Line 44, Claim 14, delete "one en" and insert -- one --

Column 29, Line 32, Claim 25, delete "$R^2$, -OH," and insert -- $R^2$ -OH, --

Column 29, Lines 37-38, Claim 25, delete "$R^{2'}$, -(NH$_2$)$_2$" and insert -- $R^{2'}$ -(NH$_2$)$_2$ --

Column 30, Line 33, Claim 26, delete "mono acrylate," and insert -- monoacrylate, --

Signed and Sealed this
Eighteenth Day of March, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,569,423 B2  
APPLICATION NO. : 12/599243  
DATED : October 29, 2013  
INVENTOR(S) : Dicke et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 952 days.

Signed and Sealed this
Twenty-second Day of September, 2015

Michelle K. Lee
*Director of the United States Patent and Trademark Office*